(12) United States Patent
Barth

(10) Patent No.: US 7,250,115 B2
(45) Date of Patent: Jul. 31, 2007

(54) NANOPORE WITH RESONANT TUNNELING ELECTRODES

(75) Inventor: Phillip W Barth, Portola Valley, CA (US)

(73) Assignee: Agilent Technologies, Inc, Santa Clara, CA (US)

( * ) Notice: Subject to any disclaimer, the term of this patent is extended or adjusted under 35 U.S.C. 154(b) by 710 days.

(21) Appl. No.: 10/462,216

(22) Filed: Jun. 12, 2003

(65) Prior Publication Data

US 2007/0138132 A1   Jun. 21, 2007

(51) Int. Cl.
*B31D 3/00* (2006.01)
*B44C 1/22* (2006.01)
*C25D 17/00* (2006.01)

(52) U.S. Cl. .......................... 216/56; 216/41; 216/67; 204/192.34

(58) Field of Classification Search ........... 204/403.01, 204/450, 451, 452, 600, 601, 603; 205/777.5, 205/778; 216/13, 41, 49, 56, 67, 96, 99, 216/100
See application file for complete search history.

(56) References Cited

U.S. PATENT DOCUMENTS

| 7,033,476 | B2* | 4/2006 | Lee et al. ................... 204/603 |
| 2002/0118027 | A1 | 8/2002 | Routkevitch et al. |
| 2004/0134778 | A1* | 7/2004 | Stelzle et al. .......... 204/403.01 |

FOREIGN PATENT DOCUMENTS

| WO | WO 00/79257 A1 | 12/2000 |
| WO | WO01/81896 | 11/2001 |
| WO | WO01/81908 | 11/2001 |
| WO | WO 02/084272 A2 | 10/2002 |

OTHER PUBLICATIONS

The European Search Report dated: Oct. 21, 2004, for Application No. EP 04010944.

* cited by examiner

*Primary Examiner*—Alex Noguerola

(57) ABSTRACT

The present invention provides an apparatus and method for making an apparatus for sensing and/or characterizing a biopolymer translocating a nanopore. The apparatus of the present invention provides a first electrode, a first insulator, a second electrode, a optional insulator, a voltage source for applying a time varying potential difference between the electrodes, and a means of measuring the resulting current between the two electrodes. A method for making the apparatus is also disclosed.

10 Claims, 17 Drawing Sheets

NANOPORE WITH RESONANT TUNNELING ELECTRODES

CROSS-REFERENCE TO RELATED APPLICATIONS

U.S. Non-Provisional application for patent Ser. No. 10/352,675 is incorporated by reference in its entirety in the current application.

TECHNICAL FIELD

The invention relates generally to the field of biopolymers and more particularly to an apparatus and method for characterizing biopolymer molecules.

BACKGROUND

Techniques for manipulating matter at the nanometer scale ("nanoscale") are important for many electronic, chemical and biological purposes (See Li et al., "Ion beam sculpting at nanometer length scales", *Nature,* 412: 166-169, 2001). Among such purposes are the desire to more quickly sequence biopolymers such as DNA. Nanopores, both naturally occurring and artificially fabricated, have recently attracted the interest to molecular biologists and biochemists for the purpose of DNA sequencing.

It has been demonstrated that a voltage gradient can drive a biopolymer such as single-stranded DNA (ssDNA) in an aqueous ionic solution through a naturally-occurring trans-substrate channel, or "nanopore," such as an α-hemolysin pore in a edgeid bilayer. (See Kasianowicz et al., "Characterization of individual polynucleotide molecules using a substrate channel", *Proc. Natl. Acad. Sci. USA,* 93: 13770-13773, 1996). The process in which the DNA molecule goes through the pore has been dubbed "translocation". During the translocation process, the extended biopolymer molecule blocks a substantial portion of the otherwise open nanopore channel. This blockage decreases the ionic electrical current flow occurring through the nanopore in the ionic solution. The passage of a single biopolymer molecule can therefore be monitored by recording the translocation duration and the decrease in current. Many such events occurring sequentially through a single nanopore provide data that can be plotted to yield useful information concerning the structure of the biopolymer molecule. For example, given uniformly controlled translocation conditions, the length of the individual biopolymer can be estimated from the translocation time.

One desire of scientists is that the individual monomers of the biopolymer strand might be identified via the characteristics of the blockage current, but this hope may be unrealized because of first-principle signal-to-noise limitations and because the naturally occurring nanopore is thick enough that several monomers of the biopolymer are present in the nanopore simultaneously.

More recent research has focused on fabricating artificial nanopores. Ion beam sculpting using a diffuse beam of low-energy argon ions has been used to fabricate nanopores in thin insulating substrates of materials such as silicon nitride (See Li et al., "Ion beam sculpting at nanometer length scales", *Nature,* 412: 166-169, 2001). Double-stranded DNA (dsDNA) has been passed through these artificial nanopores in a manner similar to that used to pass ssDNA through naturally occurring nanopores. Current blockage data obtained with dsDNA is reminiscent of ionic current blockages observed when ssDNA is translocated through the channel formed by α-hemolysin in a edgeid bilayer. The duration of these blockages is been on the millisecond scale and current reductions have been to 88% of the open-pore value. This is commensurate with translocation of a rod-like molecule whose cross-sectional area is 3-4 $nm^2$ (See Li et al., "Ion beam sculpting at nanometer length scales", *Nature,* 412: 166-169, 2001). However, as is the case with single-stranded biopolymers passing through naturally occurring nanopores, first-principle signal-to-noise considerations make it difficult or impossible to obtain information on the individual monomers in the biopolymer.

A second approach has been suggested for detecting a biopolymer translocating a nanopore in a rigid substrate material such as $Si_3N_4$. This approach entails placing two tunneling electrodes at the periphery of one end of the nanopore and monitoring tunneling current from one electrode, across the biopolymer, to the other electrode. However, it is well known that the tunneling current has an exponential dependence upon the height and width of the quantum mechanical potential barrier to the tunneling process. This dependence implies an extreme sensitivity to the precise location in the nanopore of the translocating molecule. Both steric attributes and physical proximity to the tunneling electrode could cause changes in the magnitude of the tunneling current which would be far in excess of the innate differences expected between different monomers under ideal conditions. For this reason, it is difficult to expect this simple tunneling configuration to provide the specificity required to perform biopolymer sequencing.

Resonant tunneling effects have been employed in various semiconductor devices including diodes and transistors. For instance, U.S. Pat. No. 5,504,347, Javanovic, et al., discloses a lateral tunneling diode having gated electrodes aligned with a tunneling barrier. The band structures for a resonant tunneling diode are described wherein a quantum dot is situated between two conductors, with symmetrical quantum barriers on either side of the quantum dot. The resonant tunneling diode may be biased at a voltage level whereby an energy level in the quantum dot matches the conduction band energy in one of the conductors. In this situation the tunneling current between the two conductors versus applied voltage is at a local maximum. At some other bias voltage level, no energy level in the quantum dot matches the conduction band energy in either of the conductors and the current versus applied voltage is at a local minimum. The resonant tunneling diode structure can thus be used to sense the band structure of energy levels within the quantum dot via the method of applying different voltage biases and sensing the resulting current levels at each of the different voltage biases. The different applied voltage biases can form a continuous sweep of voltage levels, and the sensed resulting current levels can form a continuous sweep of current levels. The slope of the current versus voltage can in some cases be negative. Conceptually, it is also possible to inject a known current between the conductors and measure the resulting voltage, but this approach can fail if the characteristic current versus voltage has a negative slope region. For this reason, applying a known voltage bias and sensing the resultant current is usually the preferred method.

As discussed in Nonprovisional application Ser. No. 10/352,675 referenced above, a resonant tunneling electrode arrangement can be associated with a nanopore so as to sense the presence, and energy band properties of, a biopolymer molecule extending through the nanopore. This resonant tunneling electrode arrangement provides hope of not only sensing or characterizing a biopolymer, but of identifying the constituents of the polymer and meeting the goal of rapid and efficient DNA sequencing.

Thus there is a need for specific resonant tunneling electrode structures to be associated in such an arrangement with the nanopore in order to characterize biopolymers such as DNA, a method of using such resonant tunneling electrode structures to characterize biopolymers, and methods of building such resonant tunneling electrode structures. The references cited in this application infra and supra, are hereby incorporated in this application by reference. However, cited references or art are not admitted to be prior art to this application.

SUMMARY OF THE INVENTION

The invention provides an apparatus and method for improved detection and characterization of a nanoscale moiety such as a biopolymer. The invention provides a nanopore structure for sensing a nanoscale moiety. The nanopore structure comprises a first electrode, a first insulator and a second electrode. The first electrode has a first portion of a nanopore extending there through and exposing a first electrode edge. A first insulator is adjacent to the first electrode and has a second portion of the nanopore there through and defines a first insulator edge. The first electrode edge overhangs the first insulator edge. A second electrode is adjacent to the first insulator. The second electrode has a third portion of the nanopore there through and defines a second electrode edge. The first insulator edge overhangs the second electrode edge and the first electrode and second electrode may be electrically ramped for sensing the nanoscale moiety. The invention also provides a method of fabricating a nanopore structure with nanopore for sensing a portion of a nanoscale moiety.

The method of fabrication comprises providing an electrode having a portion of a nanopore there through, the portion of the nanopore defining an electrode edge, depositing an insulator on the electrode adjacent to the nanopore, the insulator having a portion of the nanopore there through and defining an insulator edge, the insulator edge overhanging the electrode edge and depositing an electrode on the insulator adjacent to the nanopore, the electrode having a portion of the nanopore there through and defining an electrode edge, the electrode edge overhanging the insulator edge to define the nanopore structure, wherein the electrodes may be electrically ramped to sense a portion of a nanoscale moiety.

BRIEF DESCRIPTION OF THE FIGURES

The invention is described in detail below with reference to the following figures.

DETAILED DESCRIPTION OF THE INVENTION

Figure 1:
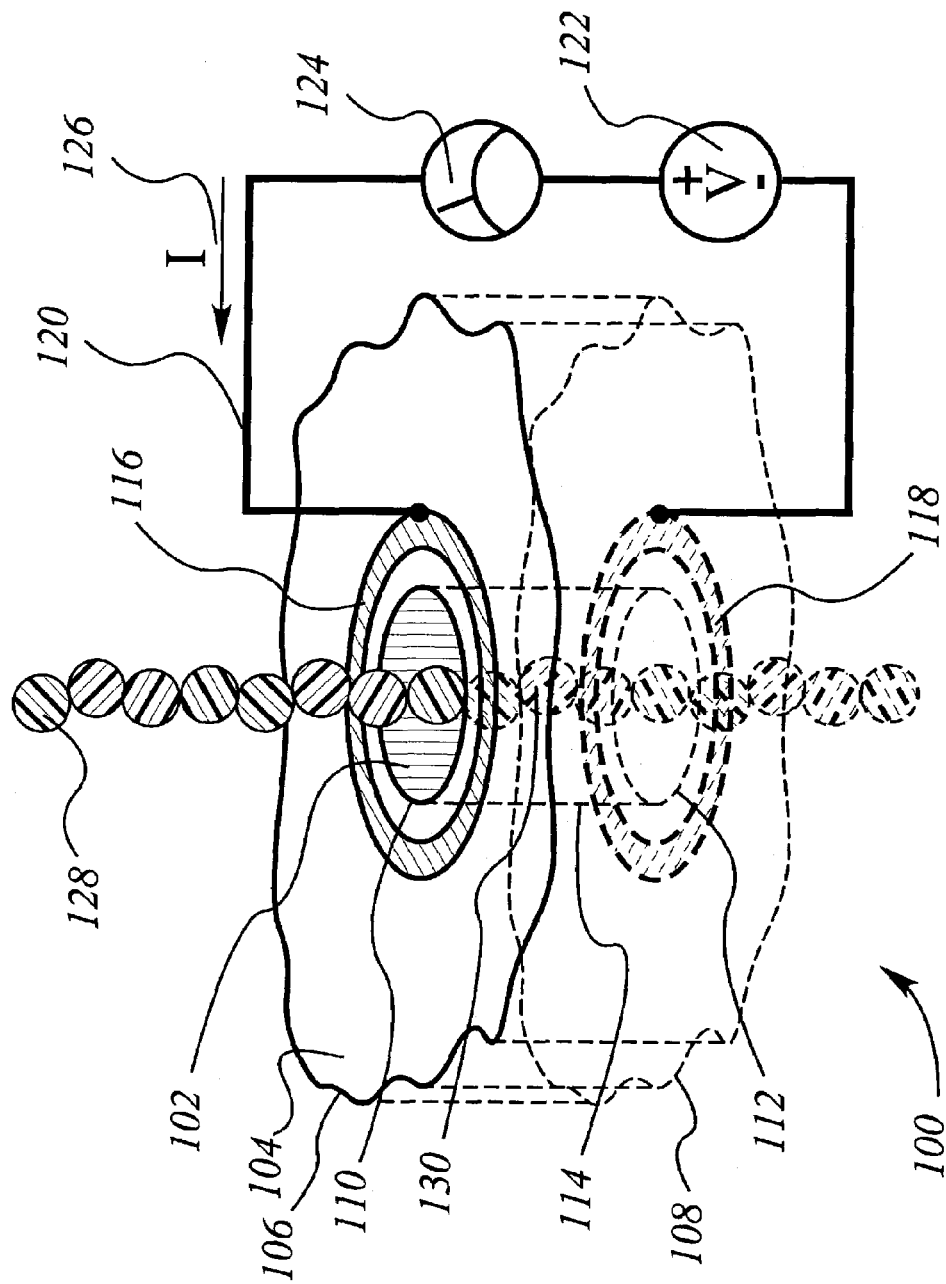
FIG. 1 illustrates a schematic representation of an embodiment 100 of the present invention.

This invention is not limited to specific compositions, methods, steps, or equipment, as such may vary. The terminology used herein is for the purpose of describing particular embodiments only, and is not intended to be limiting. Methods recited herein may be carried out in any order of the recited events that is logically possible, as well as the recited order of events. Furthermore, where a range of values is provided, it is understood that every intervening value, between the first and second limit of that range and any other stated or intervening value in that stated range is encompassed within the invention. Also, it is contemplated that any optional feature of the inventive variations described may be set forth and claimed independently, or in combination with any one or more of the features described herein.

Unless defined otherwise below, all technical and scientific terms used herein have the same meaning as commonly understood by one of ordinary skill in the art to which this invention belongs. Still, certain elements are defined herein for the sake of clarity. In the event that terms in this application are in conflict with the usage of ordinary skill in the art, the usage herein shall be controlling.

Where a range of values is provided, it is understood that each intervening value, to the tenth of the unit of the second limit unless the context clearly dictates otherwise, between the first and second limit of that range, and any other stated or intervening value in that stated range, is encompassed within the invention. The first and second limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

As used in this specification and the appended claims, the singular forms "a", "an" and "the" include plural referents unless the context clearly dictates otherwise. Thus, for example, reference to "a biopolymer" includes more than one biopolymer, and reference to "a voltage source" includes a plurality of voltage sources and the like. In describing and claiming the present invention, the following terminology will be used in accordance with the definitions set out below.

A "biopolymer" is a polymer of one or more types of repeating units. Biopolymers are typically found in biological systems and particularly include polysaccharides (such as carbohydrates), peptides (which term is used to include polypeptides and proteins), glycans, proteoglycans, edgeids, sphingoedgeids, known biologicals materials such as antibodies, etc., and polynucleotides as well as their analogs such as those compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in hydrogen bonding interactions, such as Watson-Crick type, Wobble type and the like. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. Biopolymers include DNA (including cDNA), RNA, oligonucleotides, and PNA and other polynucleotides as described in U.S. Pat. No. 5,948,902 and references cited therein (all of which are also incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (e.g., a single amino acid or nucleotide with two linking groups one or both of which may have removable protecting groups).

A "substrate" refers to any surface that may or may not be solid and which is capable of holding, embedding, attaching or which may comprise the whole or portions of an electrode.

"Hybridizing", "annealing" and "binding", with respect to polynucleotides, are used interchangeably. "Binding efficiency" refers to the productivity of a binding reaction, measured as either the absolute or relative yield of binding product formed under a given set of conditions in a given amount of time. "Hybridization efficiency" is a particular sub-class of binding efficiency, and refers to binding efficiency in the case where the binding components are polynucleotides.

It will also be appreciated that throughout the present application, that words such as "first", "second" are used in a relative sense only. A "set" may have one type of member or multiple different types. "Fluid" is used herein to reference a liquid.

The term "tunneling" refers to the change of a particle from a first position in space to a second position in space across an energy barrier region via quantum mechanical tunneling. Typically, the particle may be an electron, and the magnitude of the energy barrier may be defined as the integral of barrier height across a barrier distance.

The terms "resonance" and "resonant tunneling" refer to a quantum mechanical tunneling effect wherein the energy barriers between each of two current-carrying electrodes and a central potential well are substantially equal in magnitude. This arrangement provides for increased conductivity as compared to non-resonant tunneling across a single energy barrier of the same magnitude as either of the two energy barriers in the resonant tunneling configuration.

As regards the translocation of a biopolymer through a nanopore, the term "in" refers to being "within" and/or a portion that may also be exterior to. For instance, a biopolymer "in" a nanopore may mean that the whole biopolymer is within the opening of the nanopore or only a small portion of the biopolymer is located near the nanopore with a substantial portion protruding exterior to the nanopore.

The terms "symmetric" and "symmetrized' refer to the situation in which the tunneling barriers from each electrode to the biopolymer are substantially equal in magnitude.

The term "nanopore" refers to a pore or hole having a minimum diameter on the order of nanometers and extending through a thin substrate. Nanopores can vary in size and can range from 1 nm to around 300 nm in diameter. Most effective nanopores have been roughly around 1.5 nm to 30 nm in diameter. The thickness of the substrate through which the nanopore extends can range from 1 nm to around 700 nm.

The terms "translocation" and "translocate" refer to movement through a nanopore from one side of the substrate to the other, the movement occurring in a defined direction.

The terms "portion" and "portion of a biopolymer" refer to a part, subunit, monomeric unit, portion of a monomeric unit, atom, portion of an atom, cluster of atoms, charge or charged unit.

The term "time-varying potential" refers to an applied voltage that varies with time. The time-varying potential is produced by the "voltage source".

The term "voltage difference" refers to an electrical potential difference between any two electrodes.

The term "adjacent" refers to anything that is near, next to or adjoining. For instance, a nanopore referred to as "adjacent to an electrode" may be near an electrode, it may be next to the electrode, it may pass through an electrode or it may be adjoining the electrode. "Adjacent" can refer to spacing in linear, two-dimensional and three-dimensional space.

FIG. 1 illustrates a schematic embodiment 100 of the present invention. Nanopore 102 extends through a section of optional substrate 104. Substrate 104 has a first surface 106 and a second surface 108. First electrode edge 110 of nanopore 102 is coincident with first surface 106, and second electrode edge 112 is coincident with second surface 112. The interior wall 114 of nanopore 102 extends through the substrate 104.

First electrode 116 is adjacent nanopore 102, and second electrode 118 is adjacent nanopore 102. As illustrated, the interior diameters of first electrode 116 and second electrode 118 are greater than the interior diameter of wall 114 of nanopore 102, but this need not be the case, and the interior diameter of either electrode 116 or 118, or both, may be coincident with wall 114.

Electric circuit 120 makes contact to first electrode 116 and second electrode 118. Electric circuit 120 includes time-varying voltage source 122 and current sensing means 124 to sense the resulting current 126.

A nanoscale moiety such as a biopolymer molecule 128 is schematically depicted as a string of beads with distinct properties threaded through nanopore 102. The biopolymer molecule 128 typically resides in an ionic solvent such as aqueous potassium chloride, not shown, which also extends through nanopore 102. It should be appreciated that, due to Brownian motion if nothing else, biopolymer molecule 128 is always in motion, and such motion will result in a time-varying position of each bead within the nanopore 102. The motion of biopolymer 128 will typically be biased in one direction or another through the pore by providing an external driving force, for example by establishing an electric field through the pore from first electrode edge 110 to second electrode edge 112 in the ionic solvent by external means, not shown.

Bead 130, located near the mid-plane between first electrode edge 110 and second electrode edge 112, may be in a position wherein the magnitude of the quantum mechanical tunneling barrier from itself to first electrode 116 is equal to the magnitude of the quantum mechanical tunneling barrier from itself to second electrode 118. If it is not in such a favorable position at one instant, the combination of Brownian motion and biased motion will ensure that it has been in such a favorable position immediately beforehand, or that it will be in such a favorable position immediately afterward. In addition, at the instant when bead 130 is in the desired favorable position, the two beads adjacent to bead 130 will not be in the desired favorable position. Thus, for the instant when bead 130 is in the favorable position, rapidly varying the voltage 122 with time and measuring the resulting current 126 provides a measure of the electronic band structure of bead 130, and of equal importance, does not provide a measure of the electronic band structure of the two beads adjacent to bead 130. Thus the electronic energy band structure of bead 128 alone can be elucidated for that instant in time.

The use of additional electrodes associated with nanopore 102 is within the scope of the invention.

The biopolymer 128 may comprise a variety of shapes, sizes and materials. The shape or size of the molecule is not important, but it must be capable of translocation through the nanopore 102. For instance, both single stranded and double stranded RNA and DNA may be used as a biopolymer 128. In addition, the biopolymer 128 may contain groups or functional groups that are charged. Furthermore, metals or materials may be added, doped or intercalated within the biopolymer 128 to provide a net dipole, to provide a net charge, to provide conductivity through the biomolecule or to provide some combination of the above properties.

The first electrode 116 may comprise a variety of electrically conductive materials. Such materials include electrically conductive metals and alloys of platinum, iridium, rhodium, gold, tin, copper, zinc, iron, magnesium, cobalt, nickel, and vanadium. Other materials well known in the art that provide for electrical conduction may also be employed. When the first electrode 116 is deposited on or comprises a portion of the substrate 104, it may be positioned in any location relative to the second electrode 118 such that a potential can be established between the first electrode 116 and the second electrode 118. In addition, the bipolymer 128 must be positioned sufficiently close so that a portion of it may be sensed or characterized. In other words, the first electrode 116, the second electrode 118, and the nanopore 102 must be spaced and positioned in such a way that the biopolymer 128 may be sensed or characterized. This should not be interpreted to mean that the schematic embodiment 100 shown in FIG. 1 in any way limits the scope of the spatial orientation and positioning of each of the components of the invention. The electrodes 116 and 118 may be designed in a variety of shapes and sizes. Other electrode shapes well known in the art may be employed. In addition, parts or curved parts of rings or other shapes may be used with the invention. The electrodes may also be designed in broken format or spaced from each other. However, the design must be capable of establishing a potential difference between the first electrode 116, and the second electrode 118 in such a manner that a portion of biopolymer 128 in the process of translocating through pore 102 finds itself in the favorable position wherein resonant tunneling can occur.

The second electrode 118 may comprise the same or similar materials as described above for the first electrode 116. As discussed above, its shape, size and positioning may be altered relative to the first electrode 116 and the nanopore 3.

The optional substrate 104 may comprise a variety of materials known in the art for designing substrates and nanopores. Substrate 104 may comprise one or more layers of one or more materials including, but not limited to, membranes, edgeids, silicon nitride, silicon dioxide, platinum or other metals, silicon oxynitride, silicon rich nitride, organic polymers, and other insulating layers, carbon based materials, plastics, metals, or other materials known in the art for etching or fabricating semiconductor or electrically conducting materials. Substrate 104 need not be of uniform thickness. Substrate 104 may or may not be a solid material, and for example may comprise in part or in whole a edgeid bilayer, a mesh, wire, or other material in which a nanopore may be constructed. Substrate 104 may comprise various shapes and sizes. However, it must be large enough and of sufficient width to be capable of forming the nanopore 102 through it.

The nanopore 102 may be positioned anywhere on/through the substrate 104. The nanopore 102 may also be established by the spacing between the first electrode 116 and the second electrode 118 (in a planar or non planar arrangement). The nanopore 102 may range in size from 1 nm to as large as 300 nm. In most cases, effective nanopores for sensing or characterizing biopolymers would be in the range of around 2-20 nm. These size nanopores are just large enough to allow for translocation of a biopolymer. The nanopore 102 may be established using any methods well known in the art. For instance, the nanopore 102 may be sculpted in the substrate 104 by means of low-energy argon ion beam sculpting of an initially larger hole formed by etching or focused ion beam machining, or by sputtering, etching, photolithography, or other methods and techniques well known in the art.

The voltage source 122 may be positioned anywhere relative to the substrate 104, the nanopore 102, the first electrode 116 and the second electrode 118. The voltage source 122 should be capable of establishing a time-varying voltage difference between the first electrode 116 and the second electrode 118. A variety of voltage sources 122 may be employed consistent with the present invention. A number of these voltage sources are known in the art.

Figure 2:
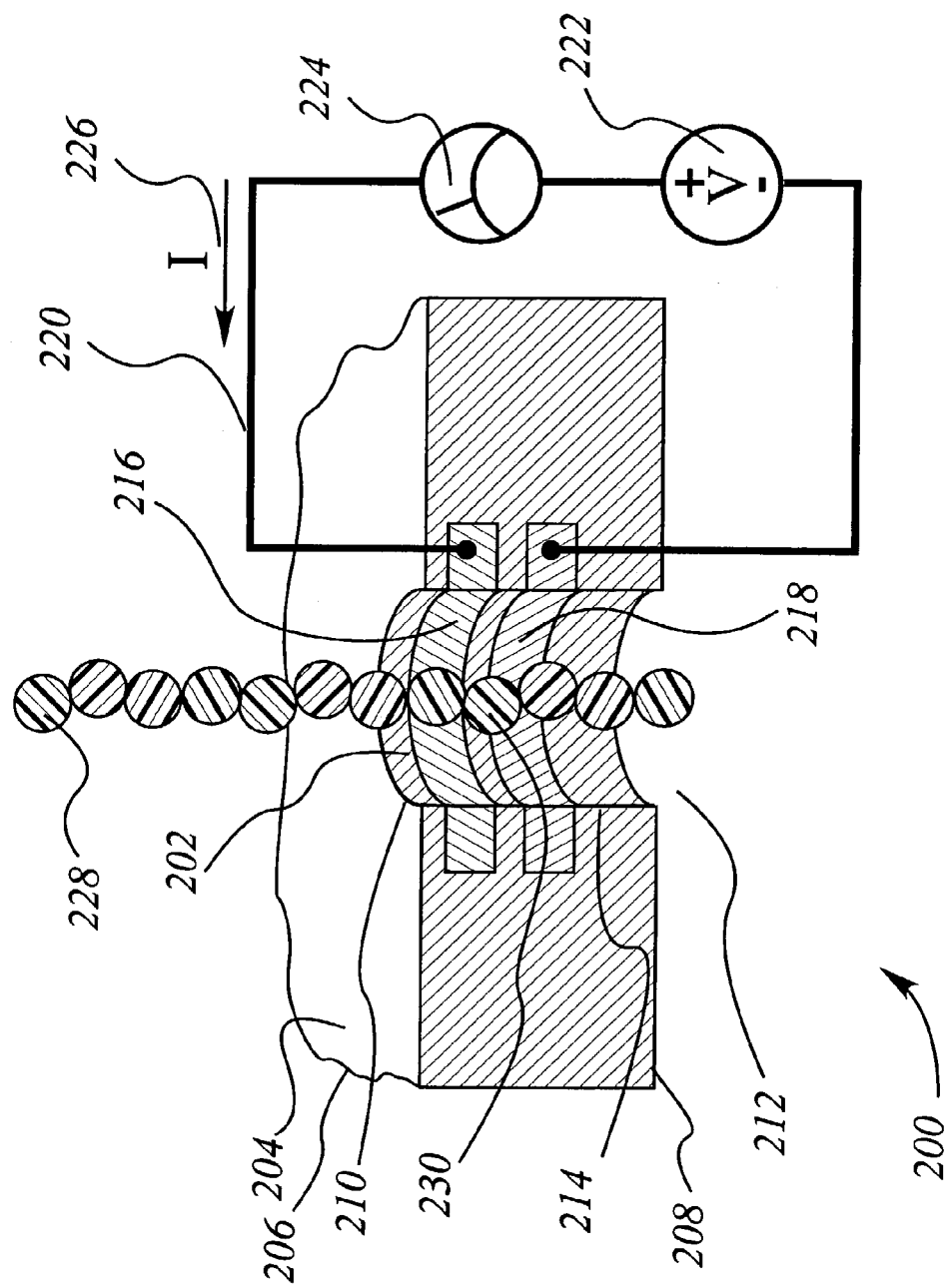
FIG. 2 illustrates a schematic representation of an embodiment 200 of the present invention.

FIG. 2 illustrates a schematic embodiment 200 of the present invention. All of the features numbered in FIG. 2 correspond to the features in FIG. 1, except that each label is incremented by one hundred (100) in comparison to the labels in FIG. 1. The drawing presents a cutaway view of the nanopore. Embodiment 200 is different from embodiment 100 in that electrodes 216 and 218 are both situated within the interior wall 214 of nanopore 202, and there is no second electrode situated on second surface 208 of substrate 204. Bead 230 may be in a favorable position between electrodes 216 and 218 for resonant tunneling to occur. Because the electrodes 216 and 218 are situated more closely together than are electrodes 116 and 118, and because electrodes 216 and 218 are each closer to bead 230 than electrodes 116 and 118 are to bead 130, embodiment 200 offers the possibility of better sensing of the properties of biopolymer molecule 228 than embodiment 100 offers for molecule 128.

Although FIG. 1 and FIG. 2 each show a pair of electrodes, the invention should not be interpreted to be limited to only this two-electrode configuration. Various electrodes of varying shapes or sizes may be employed. Furthermore, it is anticipated that the invention comprises a number of similar or different electrodes capable of tunneling in a variety of directions and space (i.e. one, two and three dimensional space).

Figure 3:
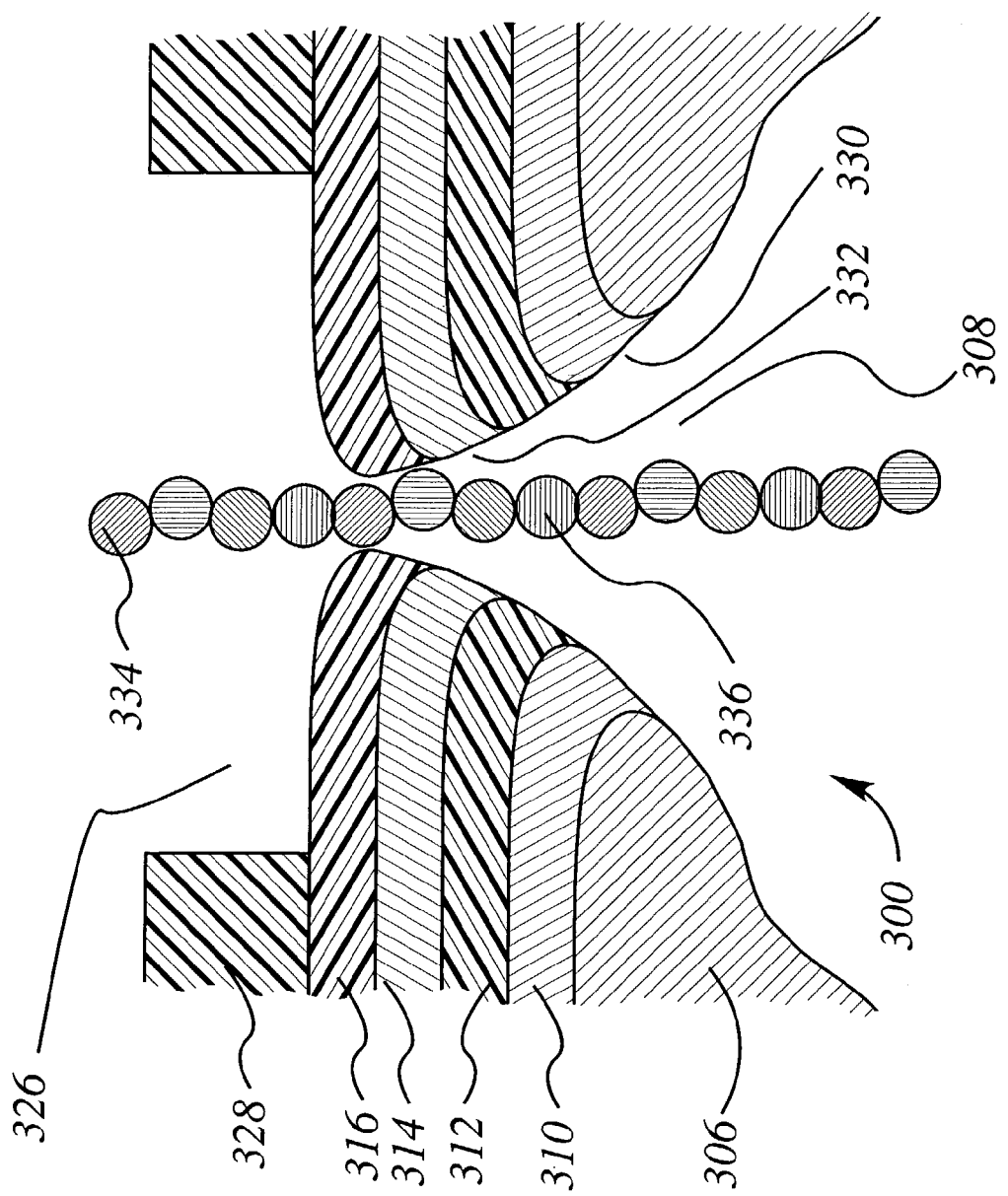
FIG. 3 illustrates a cross-sectional detail of an embodiment 300 of the present invention.

FIG. 3 illustrates a cross-sectional detail of an embodiment 300 of the present invention. Embodiment 300 is an embodiment in which the desired advantageous ring-shaped electrode structures of embodiment 200 are implemented. The fabrication process for embodiment 300 is illustrated in FIGS. 4A-4I, and the feature numbering in FIG. 3 corresponds to the feature numbering in FIGS. 4A-4I. In addition, the hatching patterns of the various layers in FIG. 3 correspond to the hatching patterns of the various layers in FIGS. 4A-4I.

As seen in FIG. 3, embodiment 300 comprises a nanopore 308 that is wide near its second end and narrow near its first end. Substrate 306 comprises a region of a material such as silicon dioxide, and the second ring-shaped electrode 310 comprises a conductor such as platinum. Second electrode 310 is formed adjacent to the nanopore 308 in a manner that surrounds the perimeter of nanopore 308. On top of second electrode 310 a first insulator 312 is formed adjacent to the nanopore 308 in a manner that surrounds the perimeter of nanopore 308 and leaves exposed a perimeter portion 330 of second electrode 310. On top of first insulator 312, a first electrode 314 is formed adjacent to the nanopore 308 in a manner that surrounds the perimeter of nanopore 308. On top of first electrode 314 is optional insulator 316. Optional insulator 316 is formed adjacent to the nanopore 308 and is placed in a manner that surrounds the perimeter of nanopore 308 and leaves exposed a perimeter portion 332 of first electrode 314. Hole 326 in primary insulator 328 provides access to the first end of the nanopore for a biopolymer molecule 334 represented schematically as a string of beads.

One particular point along the biopolymer 334 represented as bead 336 is shown in a favorable position for resonant tunneling to occur. A voltage source, not shown, applies a time-varying potential difference between electrodes 310 and 314, via a circuit, not shown, similar to that used for embodiment 100, and the resulting time-varying current is measured by a current measuring means, not shown, similar to that shown in embodiment 100, in order to characterize that portion of biopolymer molecule 334 which happens to be in the favorable position for resonant tunneling to occur.

The method of fabrication of embodiment 300 is described as follows with reference to FIGS. 3, 4A-4I, and 5A-5D. FIG. 3 is drawn to scale except for the width of hole 326 and the thickness of layer 328, both of which are drawn to a greatly reduced scale in order to fit them into the drawing. FIGS. 4A-4I are drawn to scale except that the diameter of the nanopore 308 is greatly exaggerated to make it visible at the drawing scale. FIGS. 5A-5D are not drawn to scale.

Fabrication begins by forming in a substrate 302 a composite window 304 comprising a layer of silicon nitride typically 200 nm thick on top of a layer of silicon dioxide typically 500 nm thick, both layers forming a cladding layer on the exterior surfaces of a silicon wafer. The fabrication of this window 304 is accomplished by the well-known steps of photolithography and etching of a hole in a silicon nitride layer on the bottom side of a substrate 302 such as a wafer of silicon, followed by etching of the substrate 302 in a hot aqueous caustic solution such as tetramethyl ammonium hydroxide (TMAH) in water. The caustic etching process removes the silicon beneath the window 304 but leaves the silicon dioxide and silicon nitride layers, resulting in the layout structure illustrated in FIG. 4A. Window 304 as drawn is 40 micrometers (μm) on a side, but may be larger or smaller.

Figure 4A:
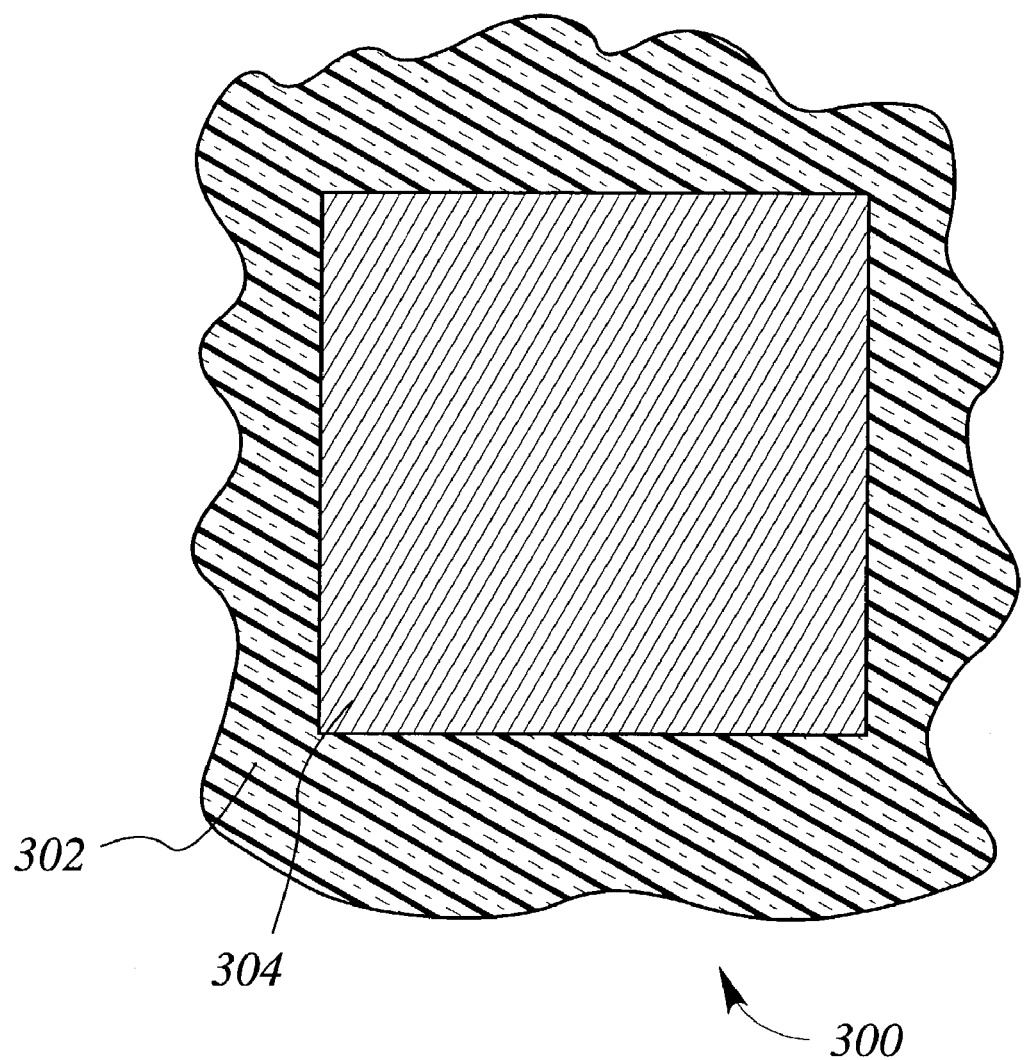
FIGS. 4A-4I illustrate sequential steps of a method of construction of embodiment 300.
Figure 4B:
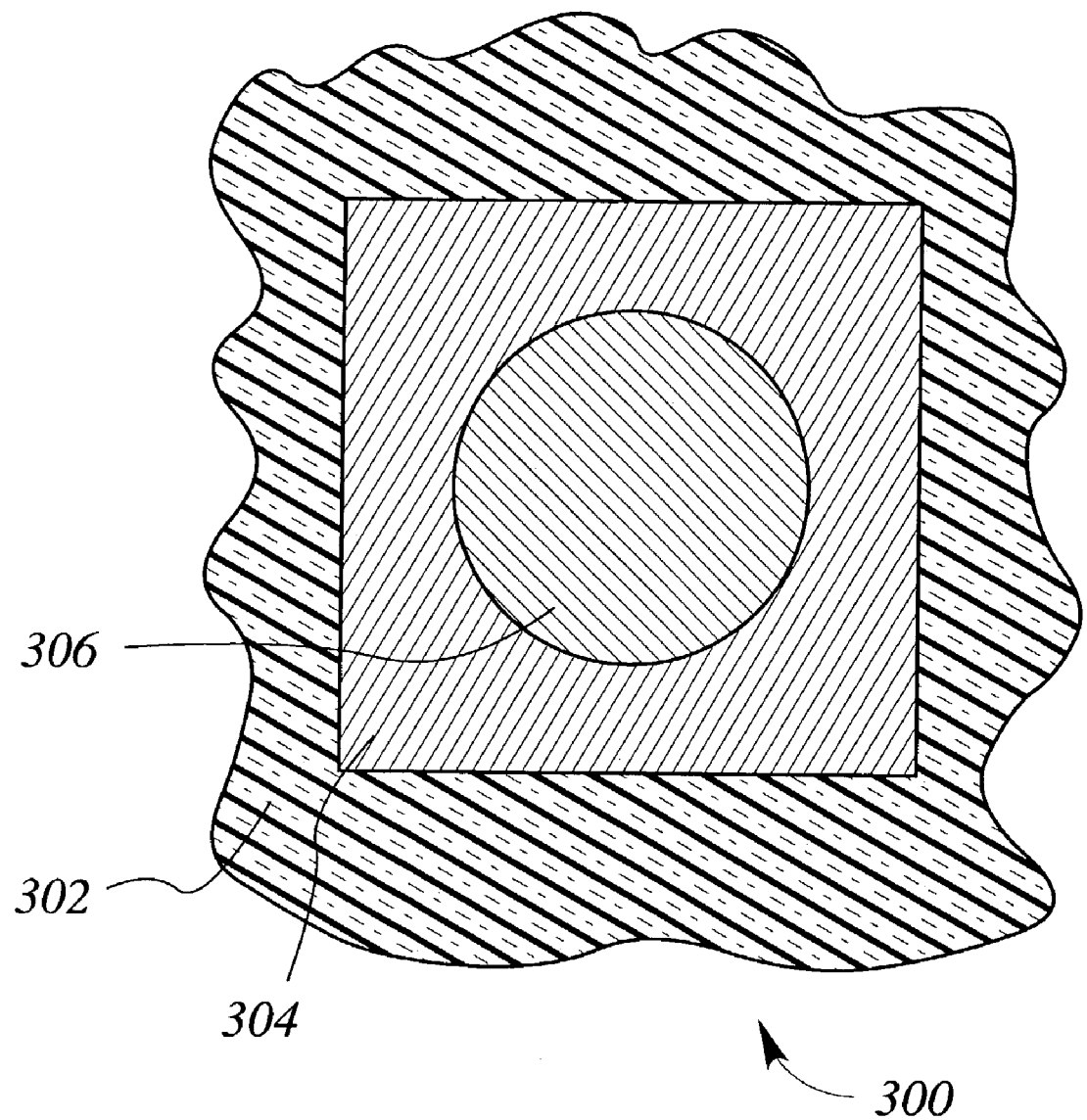

Next a photolithography step is performed to open a window in photoresist, and the silicon nitride layer is etched away to leave silicon dioxide window 306 as illustrated in FIG. 4B. This etching step is performed using well-known plasma etching techniques employing carbon tetrafluoride (CF$_4$), oxygen, and nitrogen to achieve a much faster etch rate for silicon nitride than for silicon dioxide. The technique of fabricating a silicon dioxide window region within a larger window region of silicon nitride on silicon dioxide is a separate invention, useful for obtaining a small, well-supported region of silicon dioxide with advantageous wetting properties as compared to silicon nitride.

Figure 4C:
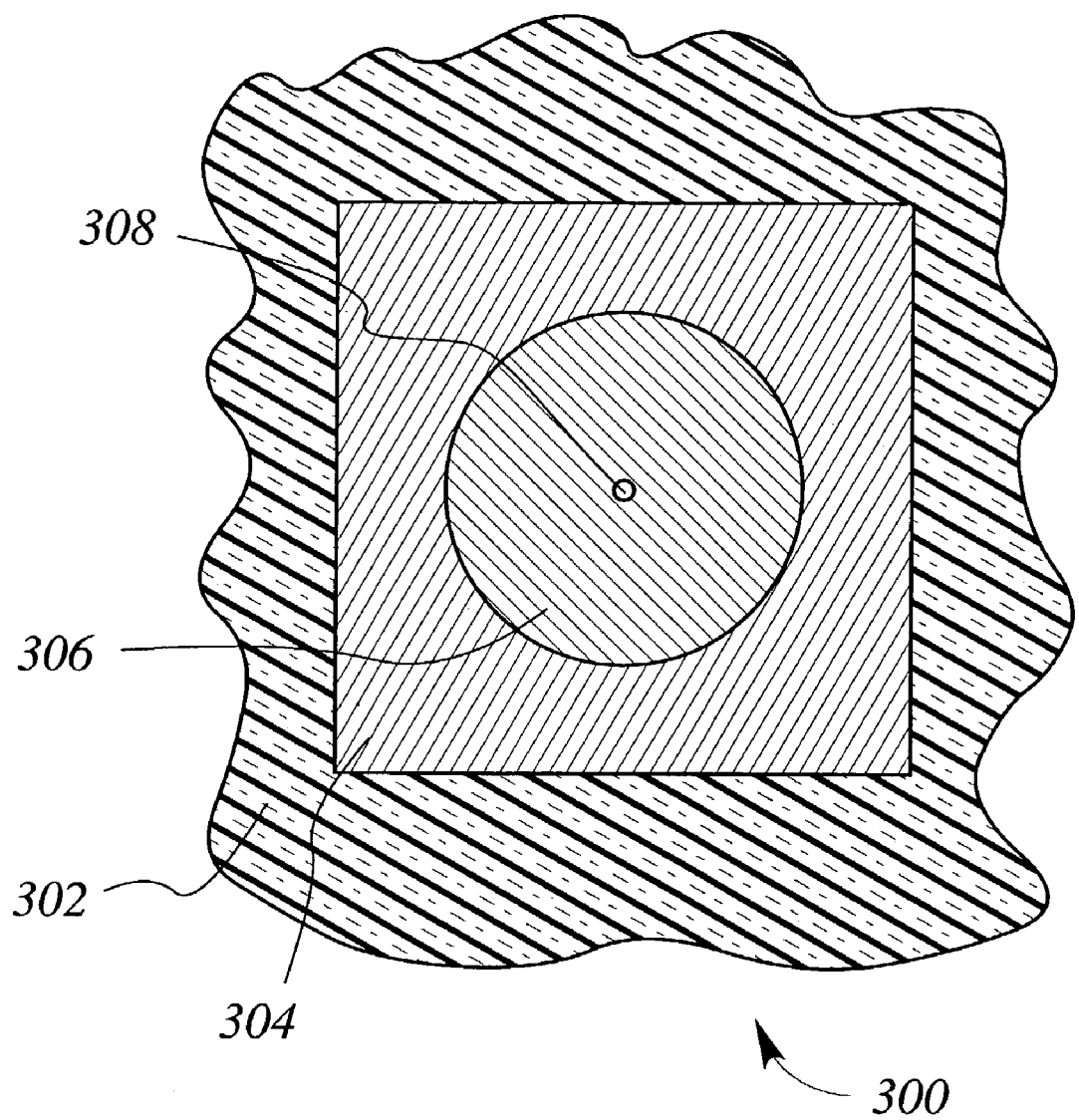

Next, drilling is performed in the center of window 306 using a focused ion beam (FIB) of gallium ions, resulting in a nanoscale hole with a diameter on the order of 50-100 nm extending through the thickness of the silicon dioxide layer. This FIB drilling process is followed by a published process of ion beam sculpting using a low energy beam of argon ions which acts to reduce the diameter of the edge of the nanoscale hole near proximate to the ion beam. This process is monitored by monitoring current of argon ions through the nanoscale hole, and is terminated when it has resulted in a nanopore 308 with a nominal diameter of 12 nm, as illustrated in FIG. 4C.

Figure 5A:
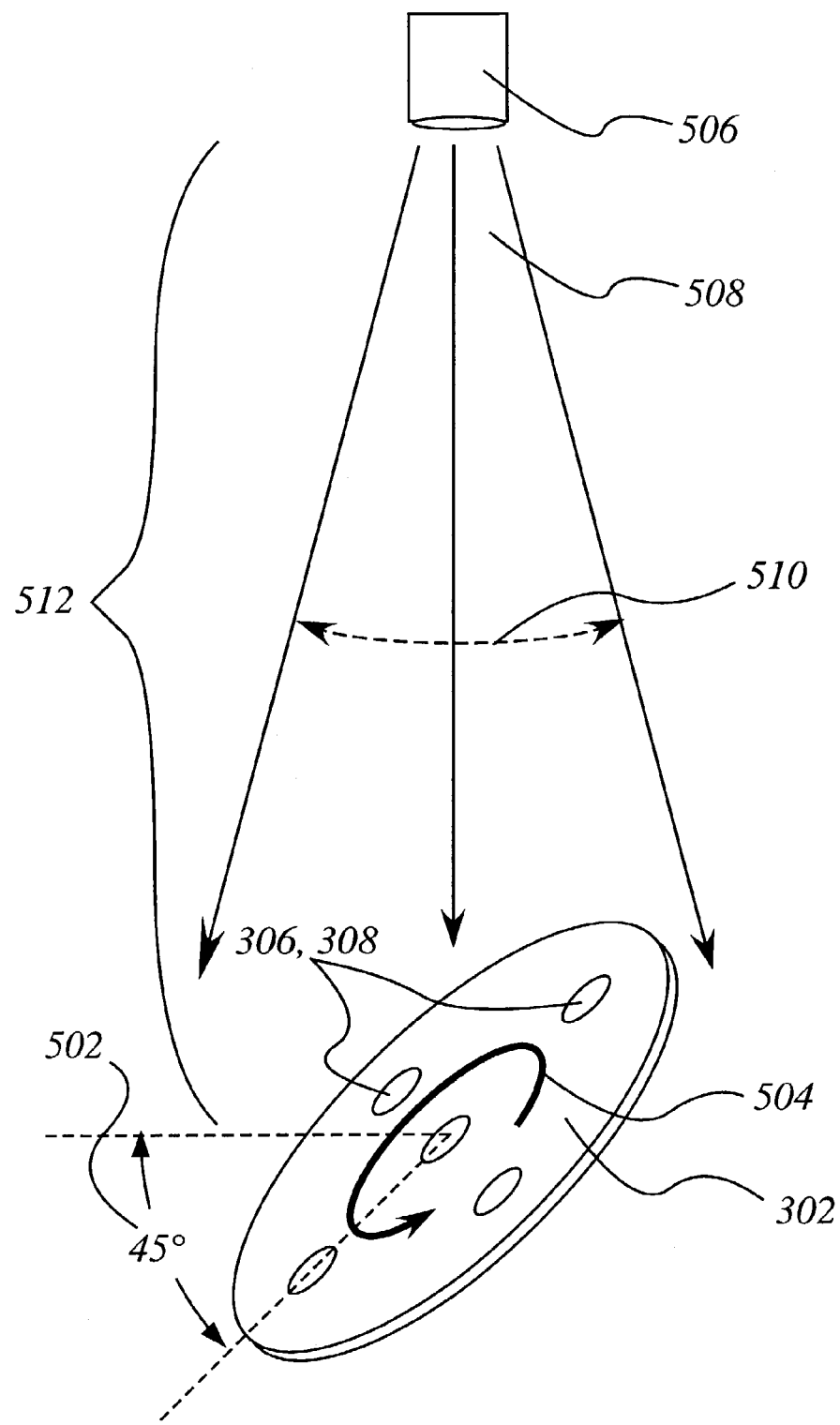
FIGS. 5A-5D illustrate the method of sequential angled line-of-sight layer deposition used in constructing embodiment 300.

Next, a process of angled line-of-sight deposition as illustrated in FIG. 5A is used to deposit a layer of material used to form second electrode 310. FIG. 5A depicts an example of substrate 302 supporting multiple instances of oxide window 306 surrounding multiple instances of nanopore 308. Substrate 302 is tilted at an angle 502 so that its surface is, for example, 45 degrees from horizontal, and is rotated in a direction 504. Deposition source 506 a typically a vacuum evaporation source or a molecular beam epitaxy source or a sputtering source, and deposition stream 508 has some angular dispersion 510 as it travels along an average deposition path length 512. The result of the tilt and the rotation is that the deposited layer resulting from deposition stream 508 overhangs the edge of nanopore 308 at region 332 shown in FIG. 3. The thickness of the layer deposited as shown in FIG. 5A is typically 2 nm, and the deposited material is typically platinum.

Figure 4D:
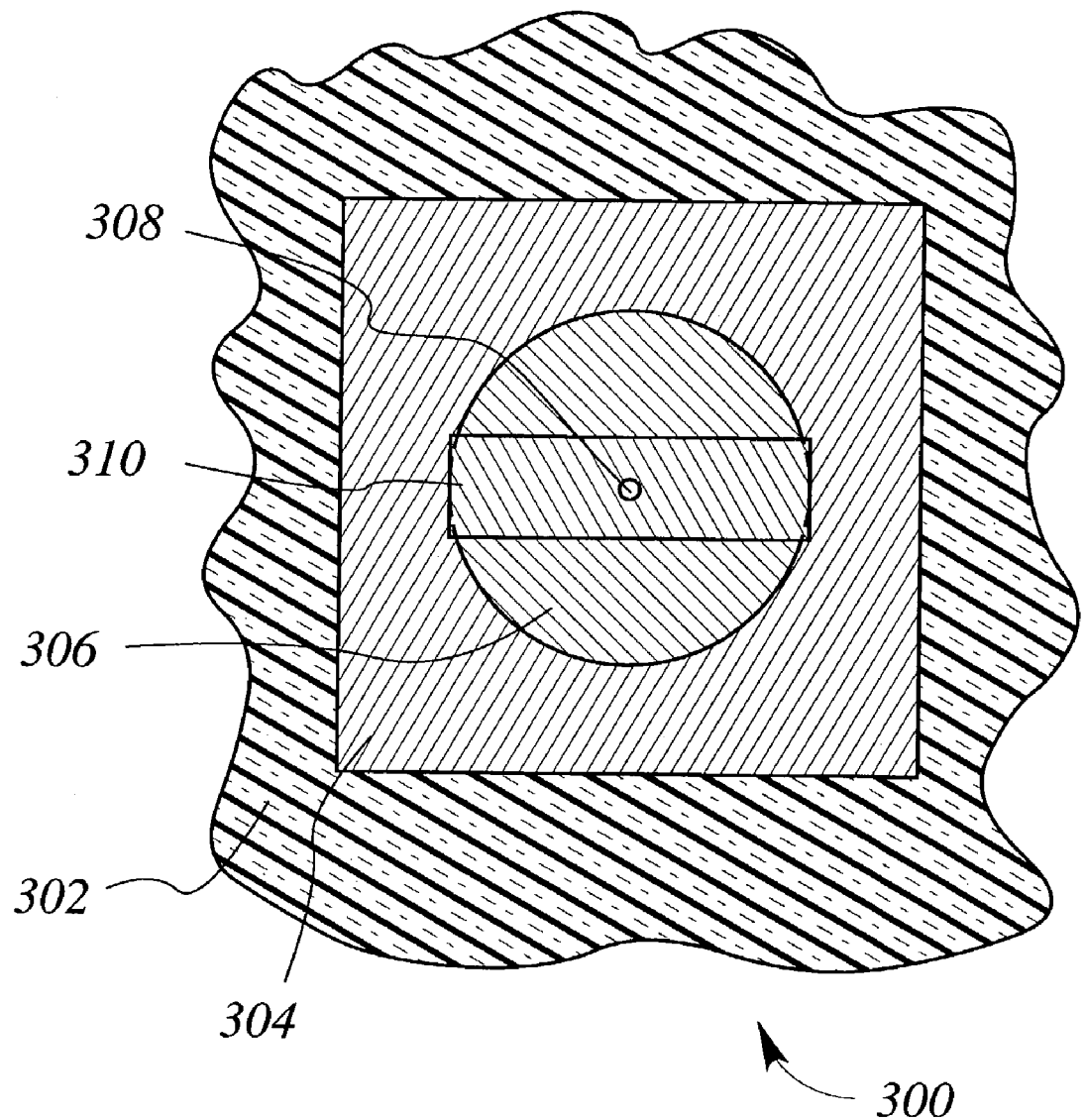

Next, a lithography step is performed, and etching is performed in a dilute solution of aqua regia, comprising a mixture of hydrochloric acid and nitric acid, to define the lateral extent of the second electrode 310 as illustrated in FIG. 4D. As drawn the electrode 310 is 5 μm wide.

Figure 5B:
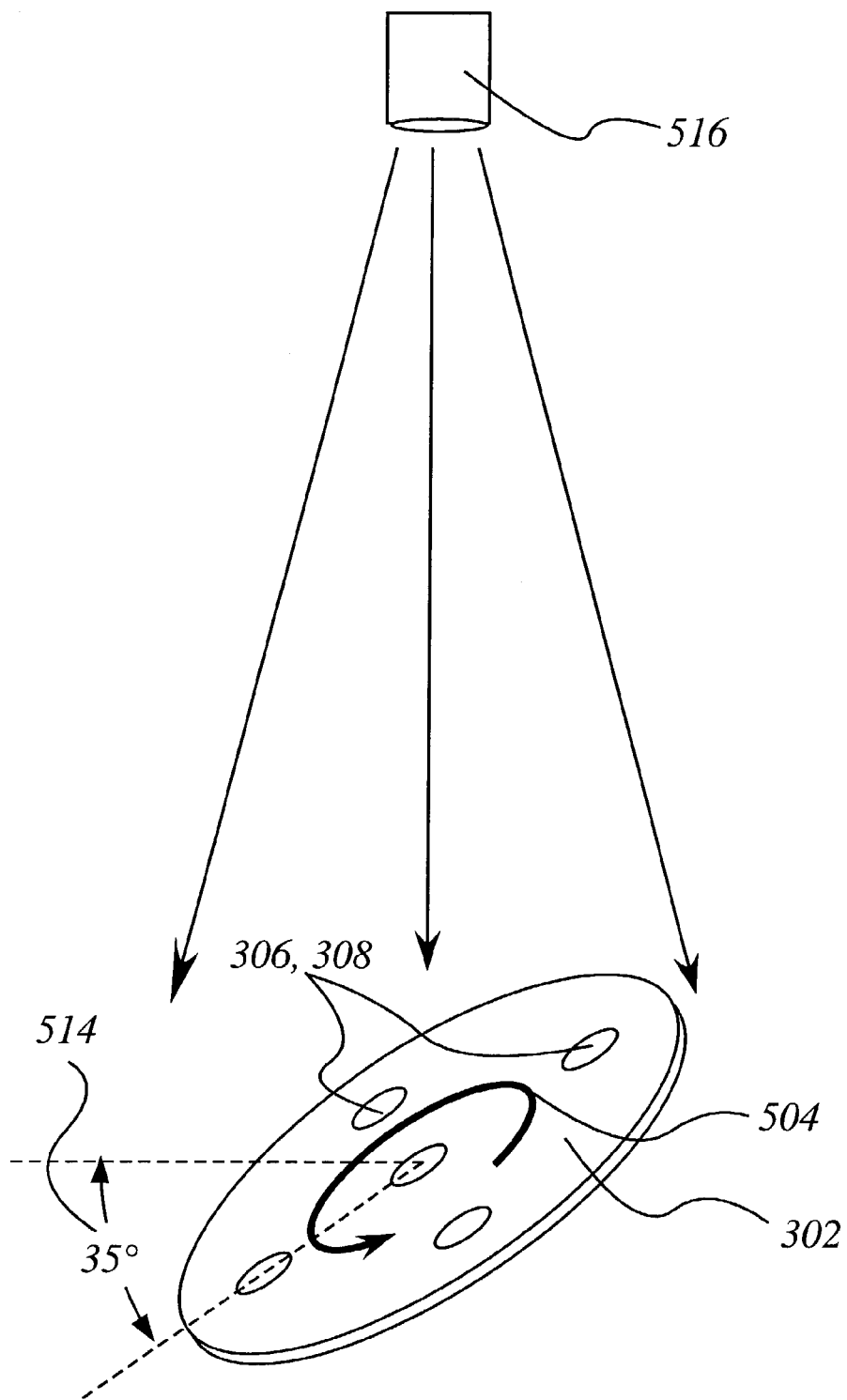

Next, a second angled line-of-sight deposition is performed as illustrated in FIG. 5B to form an insulating layer that will comprise optional insulator 312. Angle 514 is less than angle 502, for example 35 degrees, and source 516 is typically a molecular beam epitaxy source or a sputtering source. The result of the deposition step of FIG. 5B is an insulator layer, typically silicon dioxide, typically 2 nm thick, which overhangs the edge of nanopore 308 but which, as illustrated in FIG. 3, does not occlude the overhanging perimeter 330 of second electrode 310 because perimeter 330 is shadowed from the deposition stream during the line-of-sight deposition.

Figure 4E:
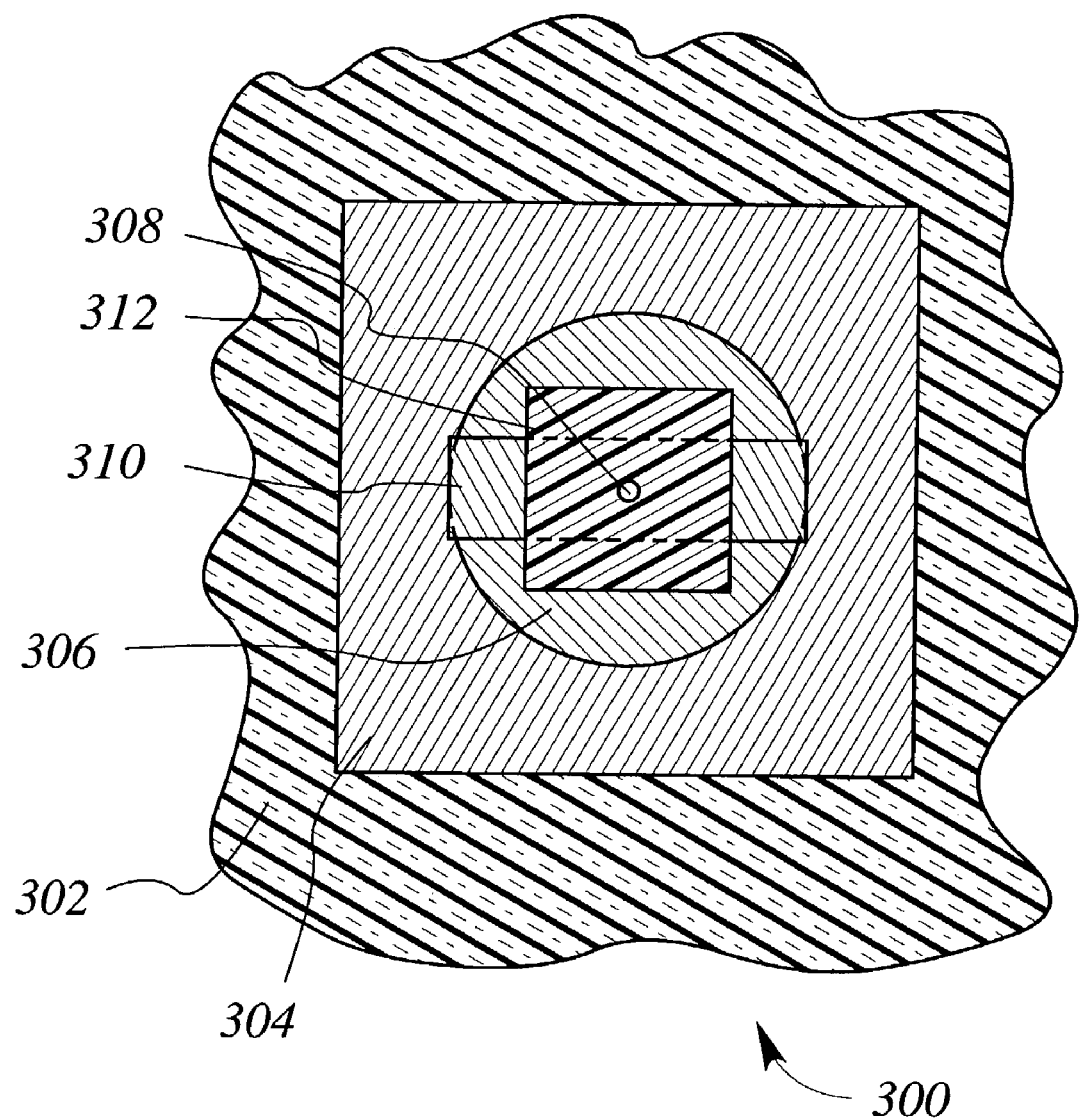

Next, a lithography step is performed and etching is performed in a dilute solution of buffered hydrofluouric acid called "buffered oxide etch" or "B.O.E," to define the lateral extent of optional insulator 312 as shown in FIG. 4E.

Figure 4F:
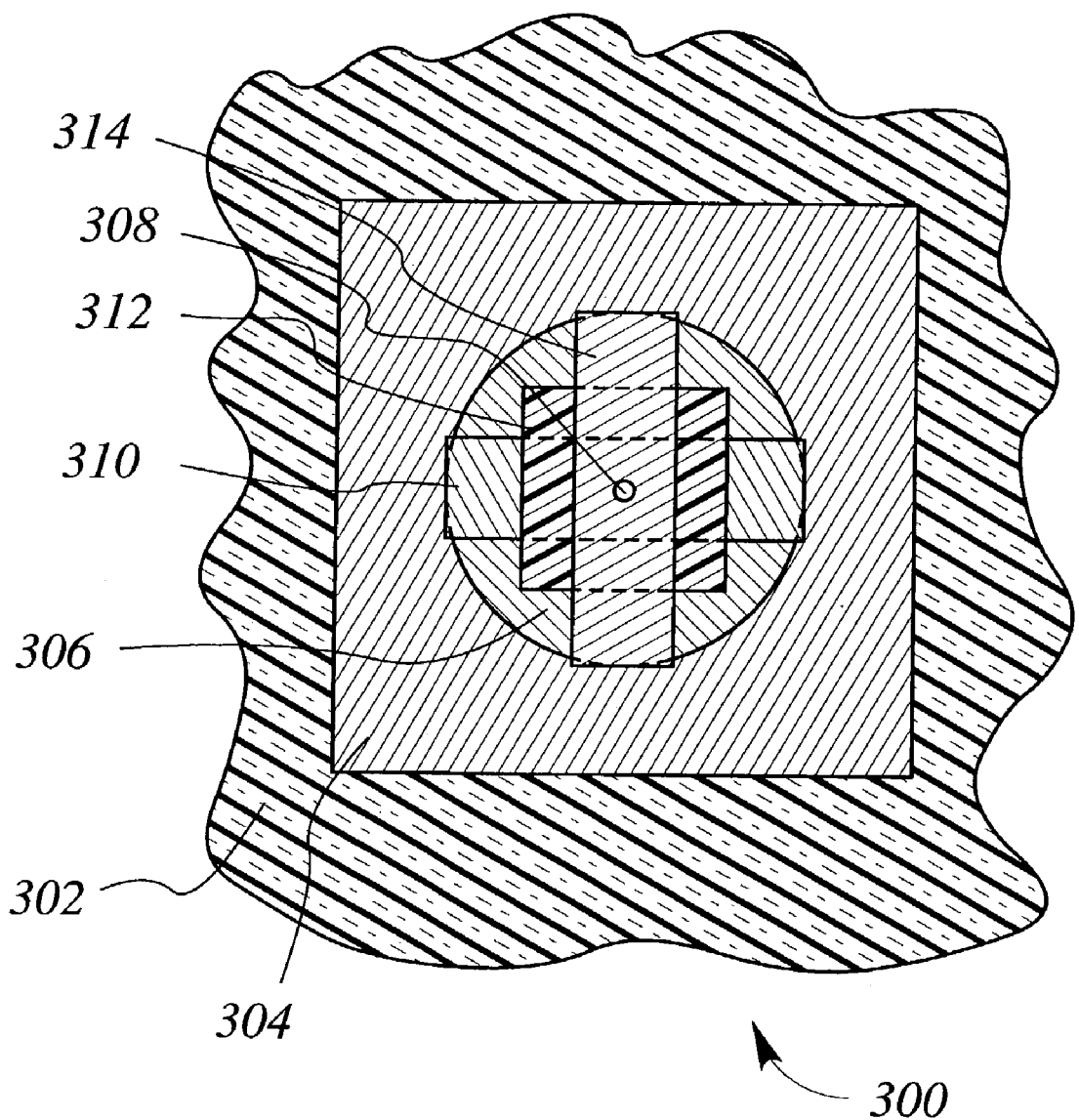
Figure 5C:
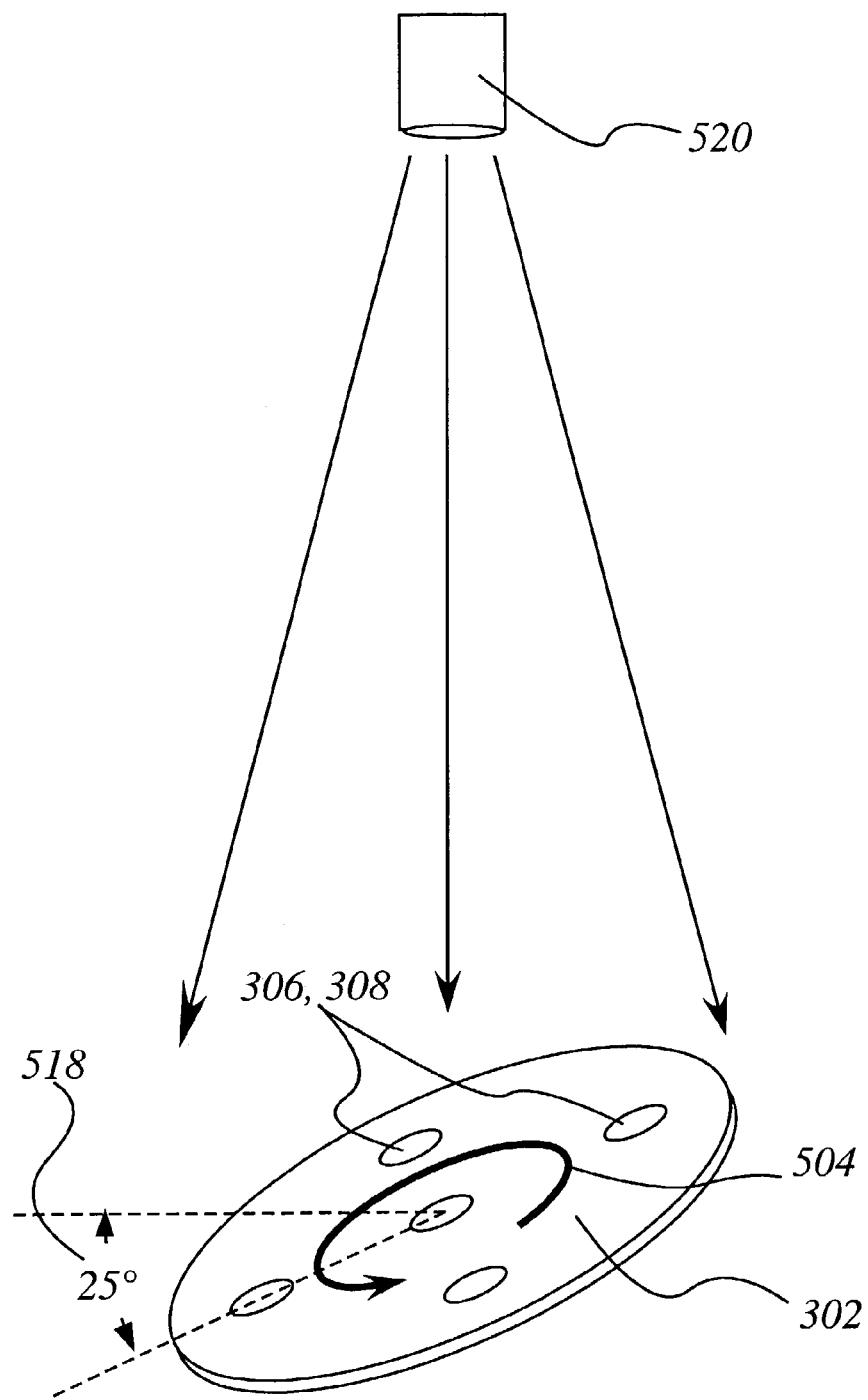

Fabrication of first electrode 314 is similar to the fabrication of second electrode 310. A conducting layer, typically comprising a 2 nm thickness of platinum, is formed by angled deposition as illustrated in FIG. 5C. Angle 518 is less than angle 514, for example 25 degrees, and source 520 is typically a vacuum evaporation source or a molecular beam epitaxy source or a sputtering source. The result of this deposition step is a layer typically 2 nm thick, typically platinum, which overhangs the edge of nanopore 308 at region 332 as illustrated in FIG. 3. Lithography and etching define the lateral extent of first electrode 314 as illustrated in FIG. 4F.

Figure 4G:
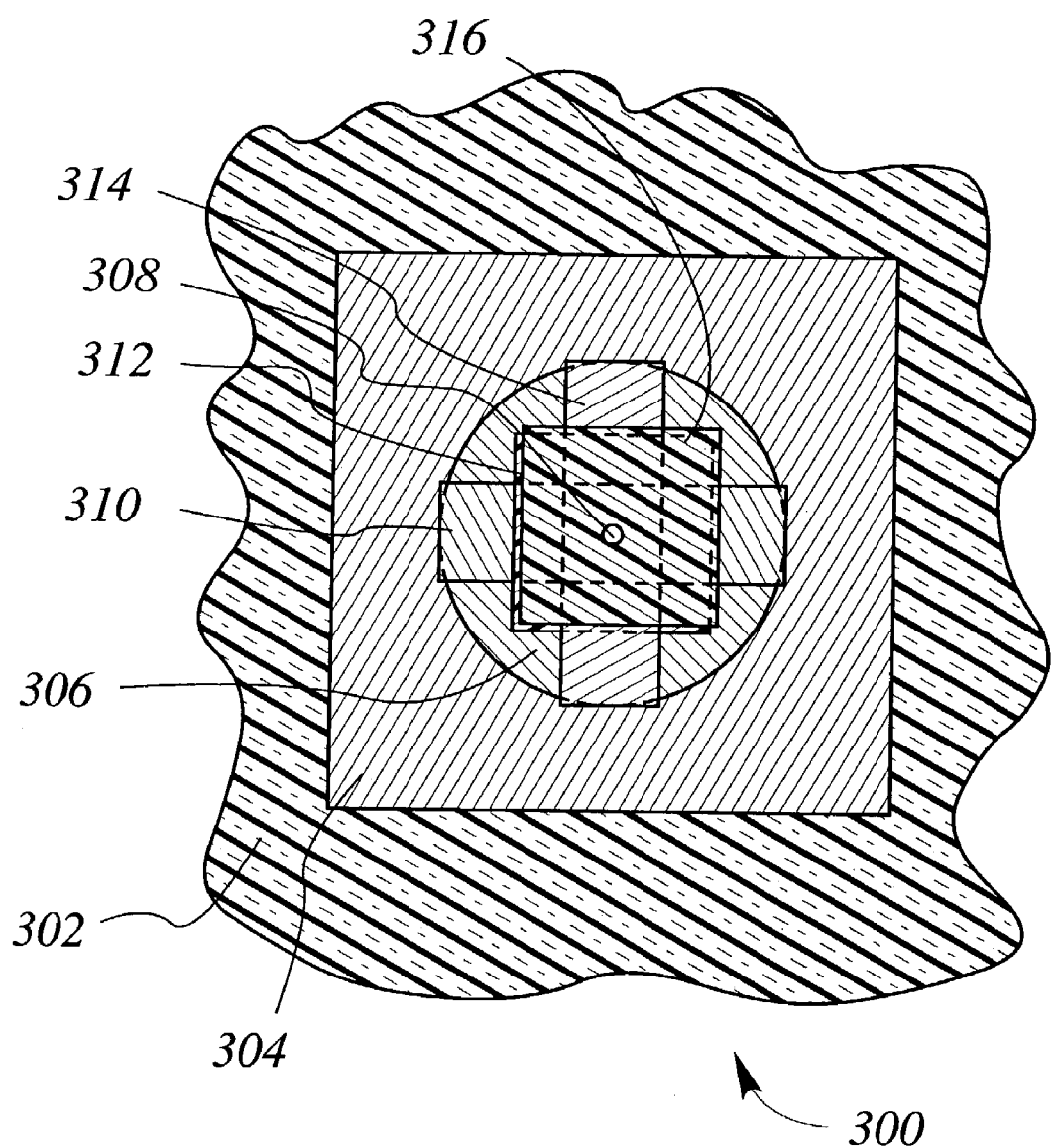
Figure 5D:
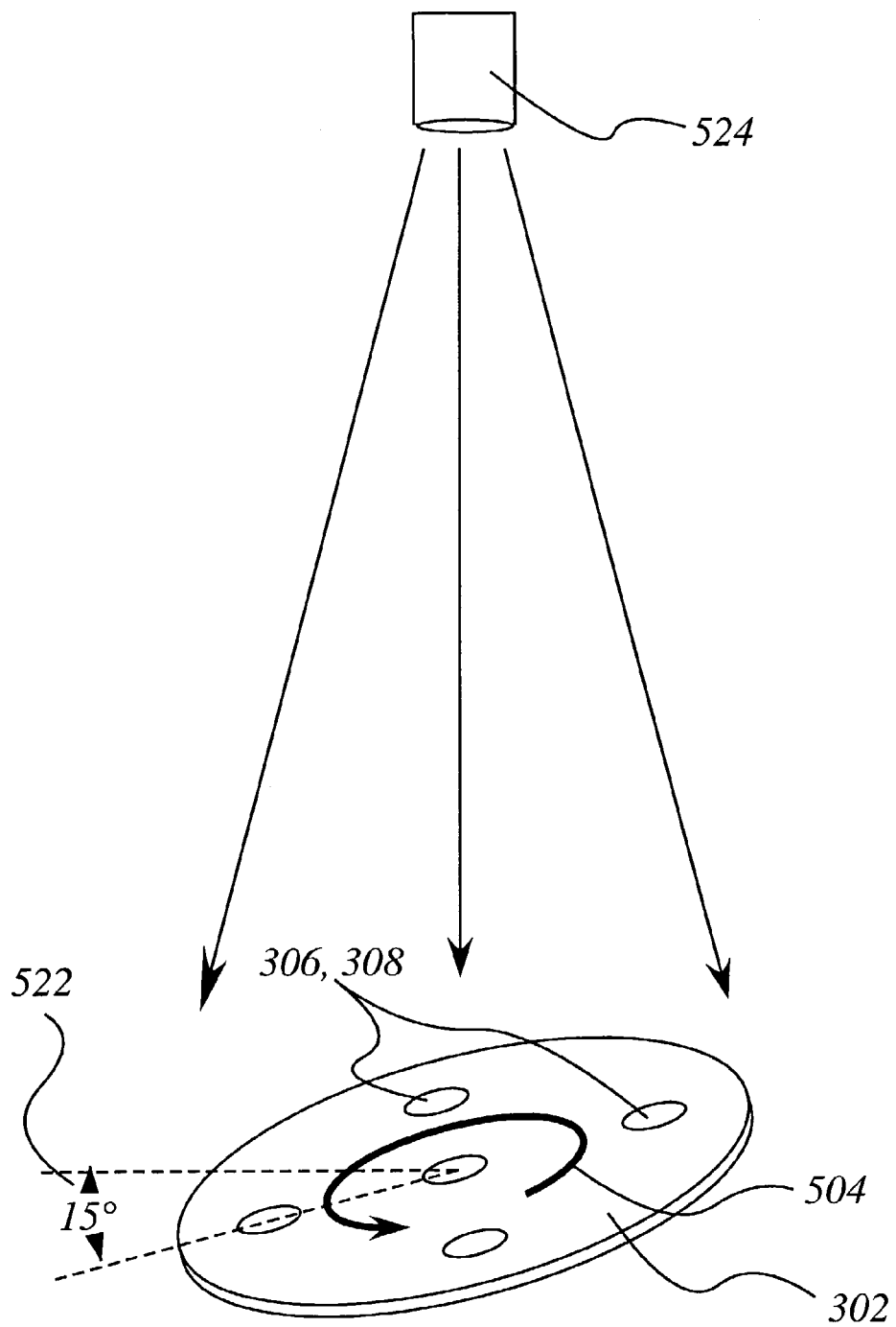

Fabrication of first insulator 316 is similar to fabrication of optional insulator 312. An insulating layer is formed by angled deposition as illustrated in FIG. 5D. Angle 522 is less than angle 518, for example 15 degrees. Source 524 is typically a molecular beam epitaxy source or a sputtering source. The result of this deposition process is a layer typically 2 nm thick, typically platinum, which overhangs the edge of nanopore 308 but which, as illustrated in FIG. 3, does not occlude overhanging perimeter 332 of first electrode 314 because perimeter 332 is shadowed from the deposition stream during the line-of-sight deposition. The lateral extent of first insulator is defined by lithography and etching as illustrated in FIG. 4G.

Figure 4H:
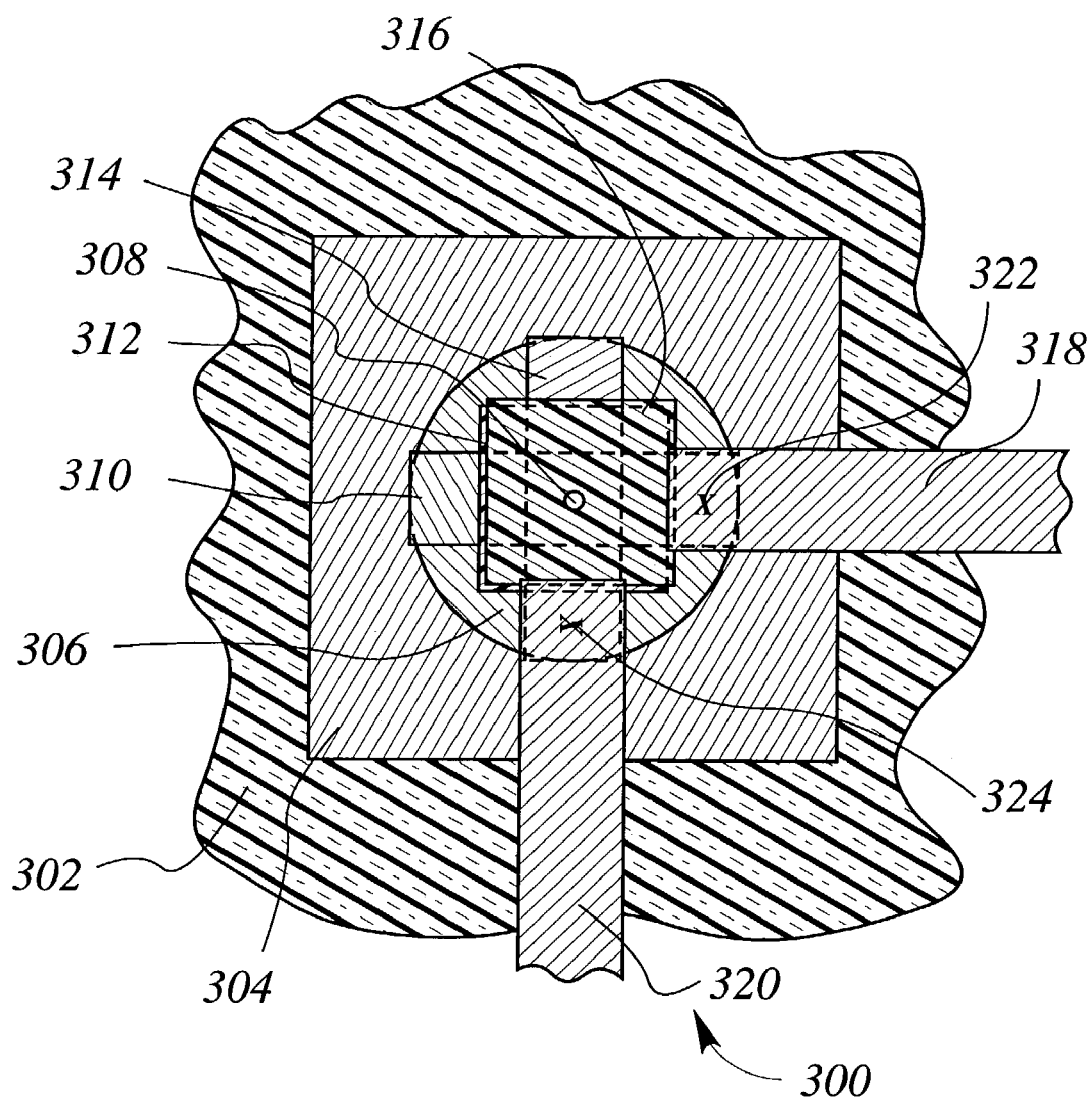
Figure 4I:
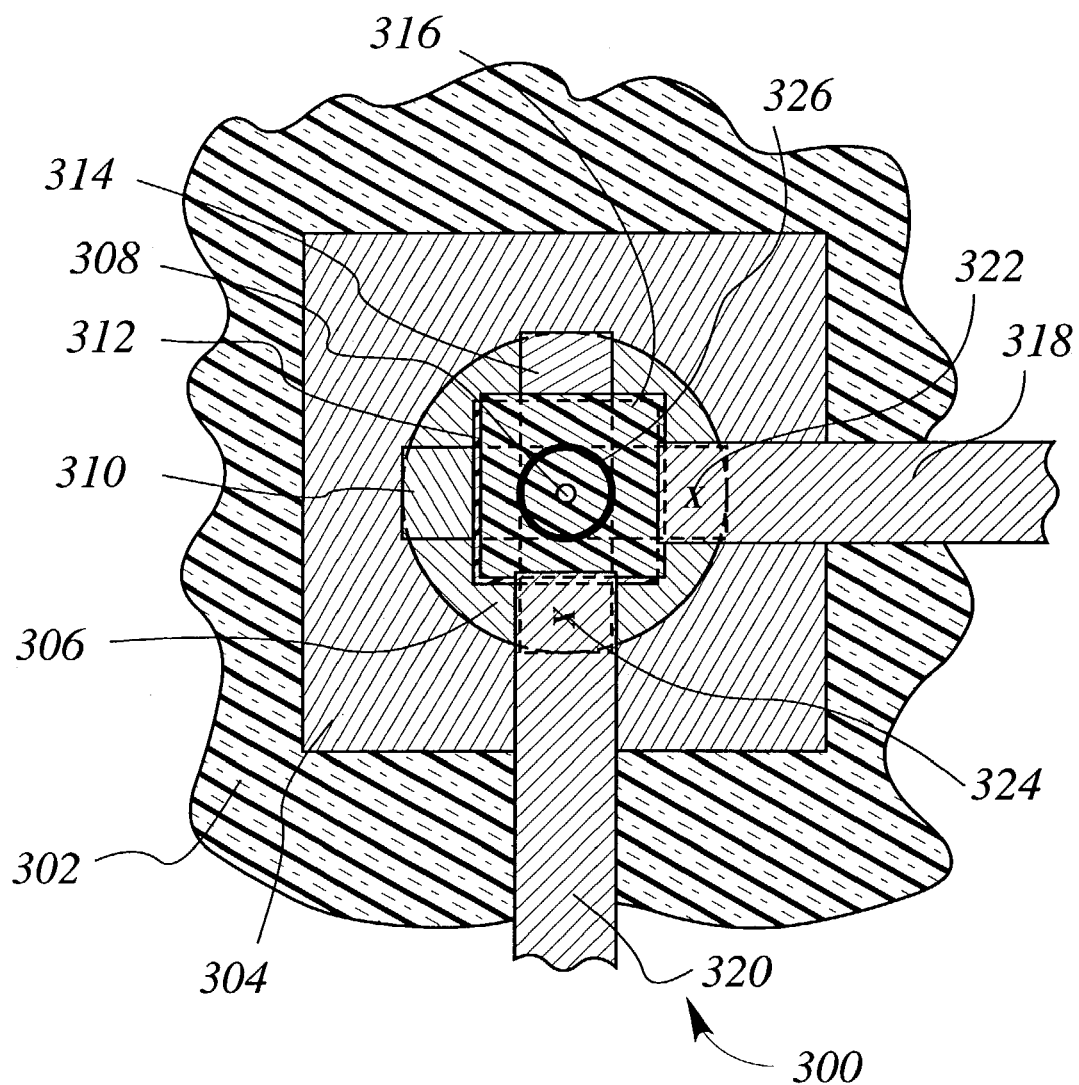

Next, as illustrated in FIG. 4H, electrical lead regions 318 and 320 are contacted to the second and first electrode regions 310 and 314 at contact regions 322 and 324. Leads 318 and 320 are formed by standard IC techniques of metal deposition and lithography, for example by electron beam deposition of an aluminum layer followed by lithography and etching. Leads 318 and 320 may extend to contact pads, not shown, which provide for electrical contact to a circuit, not shown, similar to the circuit depicted for embodiment 100.

Next a insulator layer 328 is formed, for example by spinning on a layer of a polyimide precursor and curing that precursor to form layer of polyimide insulator, in order to provide electrical insulation over leads 318 and 320 and over the ends of electrodes 310 and 314. In the region immediately over nanopore 328, lithography is performed to open hole 326 depicted in FIG. 3 and FIG. 4I, and to open contact regions over electrical contact pads, not shown.

The substrate 302 can then be diced by sawing to form individual nanopore chips, not shown, the nanopore chips can be connected to a fluidic apparatus to wet the first and second surfaces of the nanopore, and electrical connection of these chips to an electrical circuit can be performed.

It will be appreciated that the above fabrication process produces a series of edges of nanopore 308 defining a portion of the nanopore with successively smaller diameters. Each edge has an overhanging region, which can also be called a cornice, the bottom side of which is shadowed from a subsequent line-of-sight deposition so that it remains free of deposits, or nearly so. Thus, the nanopore 308 when first formed in window 306 has a fourth edge with a fourth portion of the nanopore 308 extending there through. The second electrode 310 overhangs the fourth edge, forming a third edge with a third portion of the nanopore 308 extending there through. The third portion of the nanopore is smaller than the fourth portion of the nanopore. The first insulator 312 overhangs the third edge, forming a first insulator edge with a second portion of the nanopore extending there through. The second portion of the nanopore is smaller than the third portion of the nanopore. The first electrode 314 overhangs the first insulator edge, forming a first electrode edge with a first portion of the nanopore being smaller than the second portion of the nanopore. The optional first insulator 316 overhangs the first electrode edge, forming a insulator edge with a portion of the nanopore smaller than the first portion of the nanopore. Thus, beginning with a nanopore of initially large diameter and using the techniques of successive angled line-of-sight depositions, it is possible to end with a nanopore of small diameter. As drawn in FIG. 3, the initial diameter of the nanopore at window 306 is roughly 12 nm, and the final diameter of the nanopore at first insulator 316 is 2 nm. It will be appreciated that these dimensions are representative only by way of example, and that larger and smaller nanopores can be formed by varying the diameter of the edges, the thickness and number of deposited layers, and the angles of the successive depositions.

It will be appreciated that the particular details of the above structures and fabrication processes are representative only by way of example, and are in no way intended to be limiting. Many variations in structures and materials will occur to those skilled in the art without departing from the scope and spirit of the present invention. Additional layers may be added to the nanopore structure by the obvious extension of the techniques presented herein without departing from the scope and spirit of the present invention.

It will be appreciated that the utility of the structures and processes described herein has been discussed with respect to the theory of resonant tunneling, but that the utility of these structures and processes is in no way limited to resonant tunneling, but instead applies also to other physical phenomena useful for measurement and manipulation of small object including biopolymers, including but not limited to non-resonant tunneling, electrostatic attraction and repulsion, fluidic field effect transistors, electrolysis, and the like. Either one or both of electrodes 310 and 314, or the insulator 312 between electrodes 310 and 314, might be coated with a monolayer of a molecule useful for binding to or detecting a biopolymer molecule of interest.

It will be appreciated that the electrode structures and fabrication techniques described herein have been presented with reference to the nanoscale, but that they may also possess utility at the larger microscale wherein the thicknesses of various layers are in the range of 100 nm to 25 μm.

It will be appreciated that the method of fabrication discussed above has been discussed with reference to a nanopore having a cross section similar to that in FIG. 3. However, the fabrication process is not restricted to nanopores. FIG. 3 can equally well be taken to represent a cross section through two adjacent linear edges extending into the plane of the drawing, and the fabrication method discussed above can be used to create two closely spaced line electrodes on each of the two linear edges. Likewise, either the left or the right linear edge could be absent from such a structure, leaving two closely spaced line electrodes on a single edge. Such closely spaced electrodes can have utility in a number of applications known to those skilled in various arts.

It will be appreciated that the means of line-of-sight deposition chosen for any of the steps described above, in which case there may be some undesired deposition of insulator material onto electrode region 330 or 332 or both. In such a case it may be possible to proceed with fabrication by using a known technique to remove the undesired deposition, especially of the undesired deposition is smaller in thickness than the desired layer thickness deposited on the first surface. Such known techniques for removal include, but are not limited to, chemical etching, ion beam milling, sputtering, plasma etching, and reactive ion etching.

Figure 6:
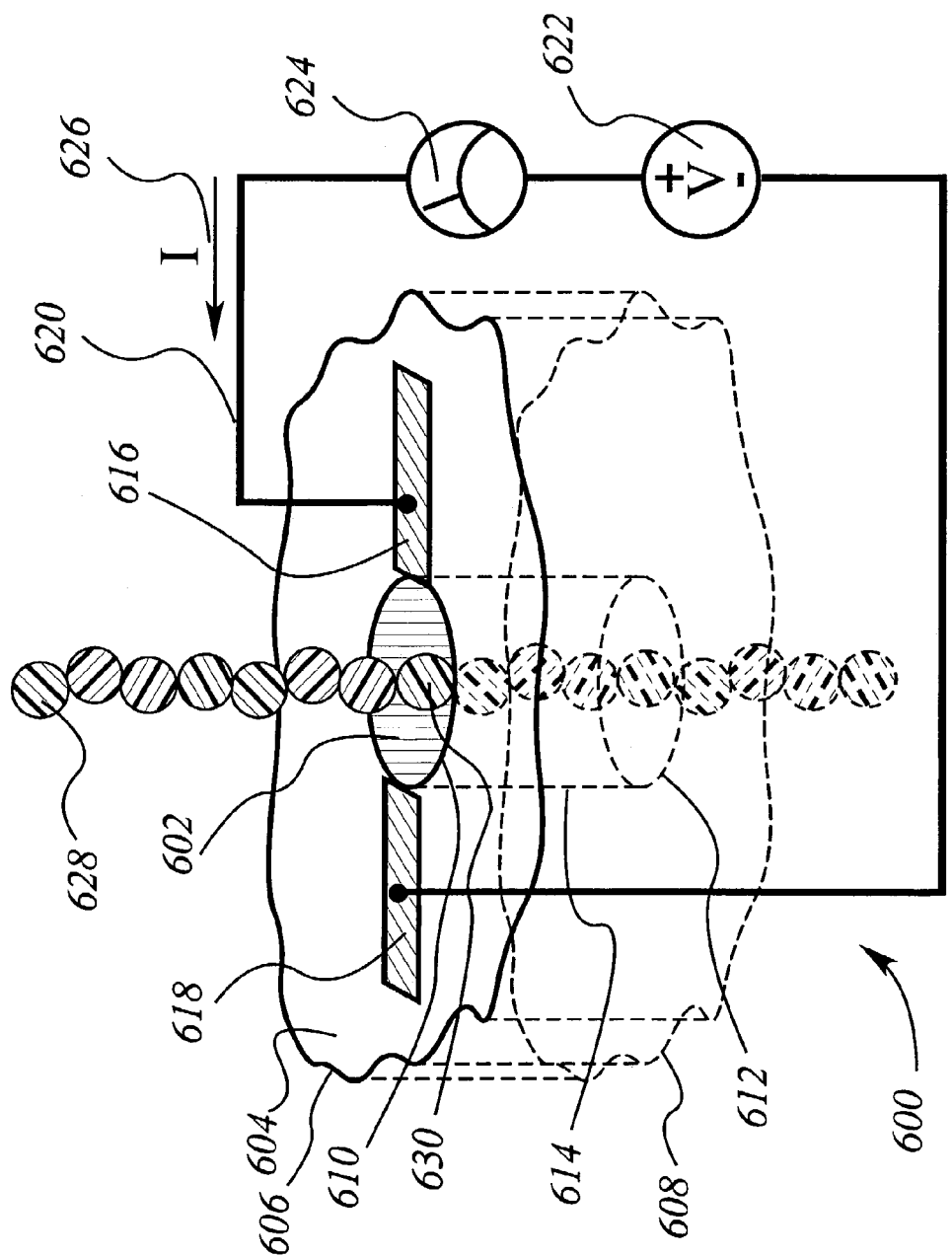
FIG. 6 illustrates an embodiment 600 of the present invention.

FIG. 6 illustrates an embodiment 600 of the present invention. All of the features numbered in FIG. 6 correspond to the features in FIG. 1, except that each label is incremented by five hundred (500) in comparison to the labels in FIG. 1. Embodiment 600 is different from embodiment 100 in that electrodes 616 and 618 are both situated on the first surface of substrate 604, and there is no second electrode situated on second surface 608 of substrate 604. Bead 630 may be in a favorable position between electrodes 616 and 618 for resonant tunneling to occur. However, because embodiment 600 does not have the advantageous ring electrode structure 116 and 118 of embodiment 100, it is less likely that the favorable conditions for resonant tunneling will occur. Thus ring electrode structure similar to those of embodiments 110, 200, and 300 are preferred.

I claim:

1. A method of fabricating a nanopore structure with nanopore for sensing a portion of a nanoscale moiety, comprising:
   (a) providing a first electrode having a portion of a nanopore there through, the portion of the nanopore defining an electrode edge;
   (b) depositing an insulator on the first electrode adjacent to the nanopore, the insulator having a portion of the nanopore there through and defining an insulator edge, the insulator edge overhanging the first electrode edge; and
   (c) depositing a second electrode on the insulator adjacent to the nanopore, the second electrode having a portion of the nanopore there through and defining the second electrode edge, the second electrode edge overhanging the insulator edge to define the nanopore structure.

2. A method of fabricating a nanopore structure as recited in claim 1, wherein at least one deposition step is performed by angled line of sight deposition.

3. A method of fabricating a nanopore structure as recited in claim 1, wherein each step is performed by angled line of sight deposition.

4. A method of making a layered nanopore structure, comprising:
   (a) providing a substrate with a surface and a portion of a nanopore there through;
   (b) tilting the substrate surface to an angle defined between horizontal and the substrate surface;
   (c) rotating the substrate at the tilted angle;
   (d) depositing a second electrode on the substrate surface adjacent to the nanopore to define a second electrode edge;
   (e) tilting the substrate surface to an angle defined between the horizontal and the substrate surface;
   (f) rotating the substrate and second electrode at the tilted angle;
   (g) depositing a first insulator on the second electrode adjacent to the nanopore to define a first insulator edge;
   (h) tilting the substrate surface at an angle defined between horizontal and the substrate surface;
   (i) rotating the substrate at the tilted angle;
   (j) depositing a first electrode on the substrate surface adjacent to the nanopore to define a first electrode edge wherein the first electrode edge, the first insulator edge and the second electrode edges define a layered nanopore structure.

5. A method as recited in claim 4, wherein the angle defined in step (b) is smaller than the angle defined in step (e).

6. A method as recited in claim 4, wherein the angle defined in step (e) is smaller than the angle defined in step (h).

7. A method as recited in claim 4, wherein the angle defined in step (b) is 45 degrees.

8. A method as recited in claim 4, wherein the angle defined in step (e) is 35 degrees.

9. A method as recited in claim 4, wherein the angled defined in step (h) is 25 degrees.

10. A method of making a layered nanopore structure, comprising:
    (a) etching a silicon substrate to form a window of silicon nitride on silicon dioxide;
    (b) etching the silicon nitride to form a window of silicon dioxide;
    (c) forming a nanopore using focused ion beam drilling followed by argon ion beam sculpting;
    (d) depositing a first electrode on the substrate adjacent to the nanopore and defining the first electrode by photolithography;
    (e) depositing a first insulator on the first electrode adjacent to the nanopore and defining the first insulator layer by photolithography;
    (f) depositing a second electrode on the first insulator adjacent to the nanopore and defining the second electrode by photolithography;
    (g) depositing an optional insulator on the second electrode adjacent to the nanopore and defining the optional insulator by photolithography;
    (h) depositing an aluminum interconnect layer on the optional insulator and defining the aluminum interconnect layer by photolithography; and
    (i) depositing an insulator substrate on the aluminum interconnect layer and defining the insulator substrate layer by photolithography.

* * * * *